United States Patent
Asako et al.

(10) Patent No.: US 11,697,605 B2
(45) Date of Patent: Jul. 11, 2023

(54) MICROBIAL FLORA ANALYSIS SYSTEM, DETERMINATION SYSTEM, MICROBIAL FLORA ANALYSIS METHOD, AND DETERMINATION METHOD

(71) Applicant: Sumitomo Chemical Company, Limited, Tokyo (JP)

(72) Inventors: Hiroyuki Asako, Osaka (JP); Fumiyoshi Okazaki, Mie (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 646 days.

(21) Appl. No.: 15/562,624

(22) PCT Filed: Mar. 30, 2016

(86) PCT No.: PCT/JP2016/060523
§ 371 (c)(1),
(2) Date: Sep. 28, 2017

(87) PCT Pub. No.: WO2016/159157
PCT Pub. Date: Oct. 6, 2016

(65) Prior Publication Data
US 2018/0105444 A1 Apr. 19, 2018

(30) Foreign Application Priority Data
Apr. 3, 2015 (JP) ................. 2015-076946

(51) Int. Cl.
| | | |
|---|---|---|
| C02F 3/00 | (2023.01) | |
| G16B 40/00 | (2019.01) | |
| G16B 20/00 | (2019.01) | |
| G16B 40/20 | (2019.01) | |
| G16B 20/20 | (2019.01) | |
| C02F 3/12 | (2023.01) | |
| C12Q 1/68 | (2018.01) | |
| C12Q 1/6888 | (2018.01) | |

(52) U.S. Cl.
CPC ............. C02F 3/006 (2013.01); C02F 3/12 (2013.01); G16B 20/00 (2019.02); G16B 20/20 (2019.02); G16B 40/00 (2019.02); G16B 40/20 (2019.02); C02F 2209/36 (2013.01); C12Q 1/68 (2013.01); C12Q 1/6888 (2013.01); Y02W 10/10 (2015.05)

(58) Field of Classification Search
None
See application file for complete search history.

(56) References Cited

U.S. PATENT DOCUMENTS

| | | |
|---|---|---|
| 2003/0108865 A1 | 6/2003 | Inoue et al. |
| 2004/0132095 A1 | 7/2004 | Iizumi et al. |
| 2012/0165215 A1 | 6/2012 | Andersen et al. |
| 2014/0058682 A1 | 2/2014 | Nasu et al. |

FOREIGN PATENT DOCUMENTS

| | | |
|---|---|---|
| CN | 1496224 A | 5/2004 |
| CN | 103348350 A | 10/2013 |
| JP | 2002-000271 A | 1/2002 |
| JP | 2004-008176 A | 1/2004 |
| JP | 2004008176 A * | 1/2004 |
| JP | 3928492 B2 | 6/2007 |
| JP | 2008-142704 A | 6/2008 |
| JP | 2012-531211 A | 12/2012 |

OTHER PUBLICATIONS

International Search Report issued in corresponding International Patent Application No. PCT/JP2016/060523 dated May 10, 2016.
International Preliminary Report on Patentability and Written Opinion issued in corresponding International Patent Application No. PCT/JP2016/060523 dated Oct. 12, 2017.
Funakoshi News, "Analysis of Microbiota by Next-Generation Sequencer with High Accuracy," http://www.funakoshi.co.jp/contents/8601, No. 557 (2014) (see partial translation).
Office Action issued in related Japanese Patent Application No. P2015-076946 dated Jan. 8, 2019.
Office Action issued in counterpart Taiwanese Patent Application No. 105110647 dated Jan. 3, 2020.
Jin, "Determination of DNA-DNA relatedness in Vibrios by means of real-time PCR," Acta HydroBiologica Sinica, 37(4):782-786 (2013).
Yang et al., "Application of Next-Generation Sequencing Technology in Analysis of Bacterial Species Composition and 16S rDNA Sequencing of Commercial Yoghurt Products," Analysis and Detection, 34 (20): 241-245 (2013) (see English abstract).
Office Action issued in counterpart Chinese Patent Application No. 201680019683.2 dated Mar. 5, 2020.
Office Action issued in counterpart Indian Patent Application No. 201747037883 dated Jan. 29, 2021.

* cited by examiner

*Primary Examiner* — Mary K Zeman
*Assistant Examiner* — Kaitlyn L Minchella
(74) *Attorney, Agent, or Firm* — Morgan, Lewis & Bockius LLP

(57) ABSTRACT

A computer of a microbial community analysis system includes an input unit configured to input a plurality of data groups including information indicating a nucleotide sequence of a gene of each of a plurality of microorganisms included in activated sludge in which a water treatment is performed; a similarity calculating unit configured to calculate a similarity between data groups on the basis of the nucleotide sequences included in the input data groups, and a coordinates calculating unit configured to calculate coordinates in a multidimensional space of each of the data groups on the basis of the calculated similarity.

8 Claims, 5 Drawing Sheets

Specification includes a Sequence Listing.

MICROBIAL FLORA ANALYSIS SYSTEM, DETERMINATION SYSTEM, MICROBIAL FLORA ANALYSIS METHOD, AND DETERMINATION METHOD

SEQUENCE LISTING SUBMISSION VIA EFS-WEB

A computer readable text file, entitled "SequenceListing.txt," created on or about Sep. 28, 2017 with a file size of about 2 kb contains the sequence listing for this application and is hereby incorporated by reference in its entirety.

TECHNICAL FIELD

The present invention relates to a microbial community analysis system and a microbial community analysis method through which microbial flora included in activated sludge in which a water treatment is performed is analyzed, and a determination system and a determination method related thereto.

BACKGROUND ART

It is desirable that wastewater in heavy and chemical industries such as chemical and steel industries which has a sufficiently reduced influence on humans and environmental organisms be discharged to the natural environment. As a wastewater treatment therefor, a biological treatment in which activated sludge which is a complex microbial system is used is performed. In order to appropriately perform a wastewater treatment, it is necessary to manage states (health states) of microbial flora which are clusters of microorganisms included in activated sludge. For example, in Patent Literature 1, in order to manage states of microbial flora, genes of microbial flora are analyzed by a T-RFLP method and states of microbial flora are plotted in a multi-dimensional space.

CITATION LIST

Patent Literature

[Patent Literature 1] Japanese Patent No. 3928492

SUMMARY OF INVENTION

Technical Problem

Plotted coordinates in the method described in Patent Literature 1 are based on electrophoretic analysis of fragmented genes. In the electrophoretic analysis, accuracy is not necessarily quantitatively and qualitatively high. Thus, the plotted coordinates indicating states of microorganisms may not necessarily be accurate. That is, in the method described in Patent Literature 1, it is difficult to analyze microbial florae with sufficient accuracy.

The present invention has been made in view of the above circumstances, and provides a microbial community analysis system and a microbial community analysis method through which it is possible to analyze microbial florae included in activated sludge in which a water treatment is performed accurately, and a determination system and a determination method related thereto.

Solution to Problem

In order to achieve the above object, a microbial community analysis system according to an embodiment of the present invention includes input means configured to input a plurality of data groups including information indicating a nucleotide sequence of a gene of each of a plurality of microorganisms included in activated sludge in which a water treatment is performed; similarity calculating means configured to calculate a similarity between data groups on the basis of the nucleotide sequences included in the data groups input by the input means; and coordinates calculating means configured to calculate coordinates in a multidimensional space of each of the data groups on the basis of the similarity calculated by the similarity calculating means.

In the microbial community analysis system according to the embodiment of the present invention, coordinates in a multidimensional space are calculated on the basis of the nucleotide sequence of the gene of each of the plurality of microorganisms constituting microbial flora. Analysis based on nucleotide sequences is more accurate than electrophoretic analysis quantitatively and qualitatively. Thus, the coordinates calculated by the microbial community analysis system according to the embodiment of the present invention represent states of microbial flora accurately compared to when electrophoretic analysis is used. That is, according to the microbial community analysis system in the embodiment of the present invention, it is possible to analyze microbial flora accurately.

The microbial community analysis system may further include determination rule generating means configured to generate a determination rule for determining states of a plurality of microorganisms from a nucleotide sequence of a gene of each of the plurality of microorganisms included in activated sludge in which a water treatment is performed on the basis of the coordinates calculated by the coordinates calculating means. In such a configuration, for example, it is possible to generate a determination rule for determining whether the microbial flora is in a normal state (healthy state). As described above, since the coordinates calculated by the microbial community analysis system according to the embodiment of the present invention represent states of microbial flora accurately, it is possible to perform determination accurately according to the determination rule.

The input means may input the data group including information indicating an abundance proportion of each of the plurality of microorganisms. The similarity calculating means may calculate a similarity between data groups on the basis of information indicating abundance proportions included in the data group input by the input means. In such a configuration, coordinates can represent states of microbial flora more accurately.

The microbial community analysis system may further include reading means configured to read nucleotide sequences of genes from the plurality of microorganisms included in the activated sludge, and data generating means configured to generate the data group based on the nucleotide sequences of genes read by the reading means and input the generated data group to the input means. In such a configuration, it is possible to reliably input the data group including information indicating nucleotide sequences and it is possible to reliably implement an embodiment of the present invention.

The determination system according to the embodiment of the present invention is a determination system configured to determine states of a plurality of microorganisms from a nucleotide sequence of gene of each of the plurality of microorganisms included in activated sludge in which a water treatment is performed based on a determination rule generated by the microbial community analysis system according to the embodiment of the present invention. The determination system includes input means configured to input a data group including information indicating a nucleotide sequence of a gene of each of a plurality of determination target microorganisms; similarity calculating means configured to calculate a similarity between a determination target data group and a data group used to generate the determination rule on the basis of nucleotide sequences included in the determination target data group input by the input means; coordinates calculating means configured to calculate coordinates in a multidimensional space of the determination target data group on the basis of the similarity calculated by the similarity calculating means; and determining means configured to determine states of the plurality of microorganisms from coordinates of the determination target data group calculated by the coordinates calculating means based on the determination rule generated by the microbial community analysis system. According to the determination system in the embodiment of the present invention, it is possible to perform determination based on the determination rule generated by the microbial community analysis system.

Note that descriptions of the present invention include not only the microbial community analysis system and the determination system described above but also a microbial community analysis method and a determination method which will be described below. These are different only in category and are substantially the same invention with the same operations and effects.

That is, a microbial community analysis method according to an embodiment of the present invention is a method of operating a microbial community analysis system. The microbial community analysis method includes an input step of inputting a plurality of data groups including information indicating a nucleotide sequence of a gene of each of a plurality of microorganisms included in activated sludge in which a water treatment is performed; a similarity calculating step of calculating a similarity between data groups on the basis of the nucleotide sequences included in the data groups input in the input step; and a coordinates calculating step of calculating coordinates in a multidimensional space of each of the data groups on the basis of the similarity calculated in the similarity calculating step.

In addition, a determination method according to an embodiment of the present invention is a method of operating a determination system configured to determine states of a plurality of microorganisms from a nucleotide sequence of gene of each of the plurality of microorganisms included in activated sludge in which a water treatment is performed based on a determination rule generated by the microbial community analysis system according to the embodiment of the present invention. The determination method includes an input step of inputting a data group including information indicating a nucleotide sequence of a gene of each of a plurality of determination target microorganisms; a similarity calculating step of calculating a similarity between a determination target data group and a data group used to generate the determination rule on the basis of nucleotide sequences included in the determination target data group input in the input step; a coordinates calculating step of calculating coordinates in a multidimensional space of the determination target data group on the basis of the similarity calculated in the similarity calculating step; and a determining step of determining states of the plurality of microorganisms from coordinates of the determination target data group calculated in the coordinates calculating step based on the determination rule generated by the microbial community analysis system.

Advantageous Effects of Invention

In the embodiment of the present invention, coordinates in a multidimensional space are calculated on the basis of a nucleotide sequence of a gene of each of a plurality of microorganisms constituting microbial flora. Analysis based on nucleotide sequences is more accurate than electrophoretic analysis quantitatively and qualitatively. Thus, the coordinates calculated according to the microbial community analysis system in the embodiment of the present invention represent states of microbial florae accurately compared to when electrophoretic analysis is used. That is, according to the embodiment of the present invention, it is possible to analyze microbial flora accurately.

DESCRIPTION OF EMBODIMENTS

A microbial community analysis system, a determination system, a microbial community analysis method and a determination method according to embodiments of the present invention will be described below in detail with reference to the drawings. Here, in description of the drawings, the same components are denoted by the same reference numerals and redundant descriptions will be omitted.

Figure 1:
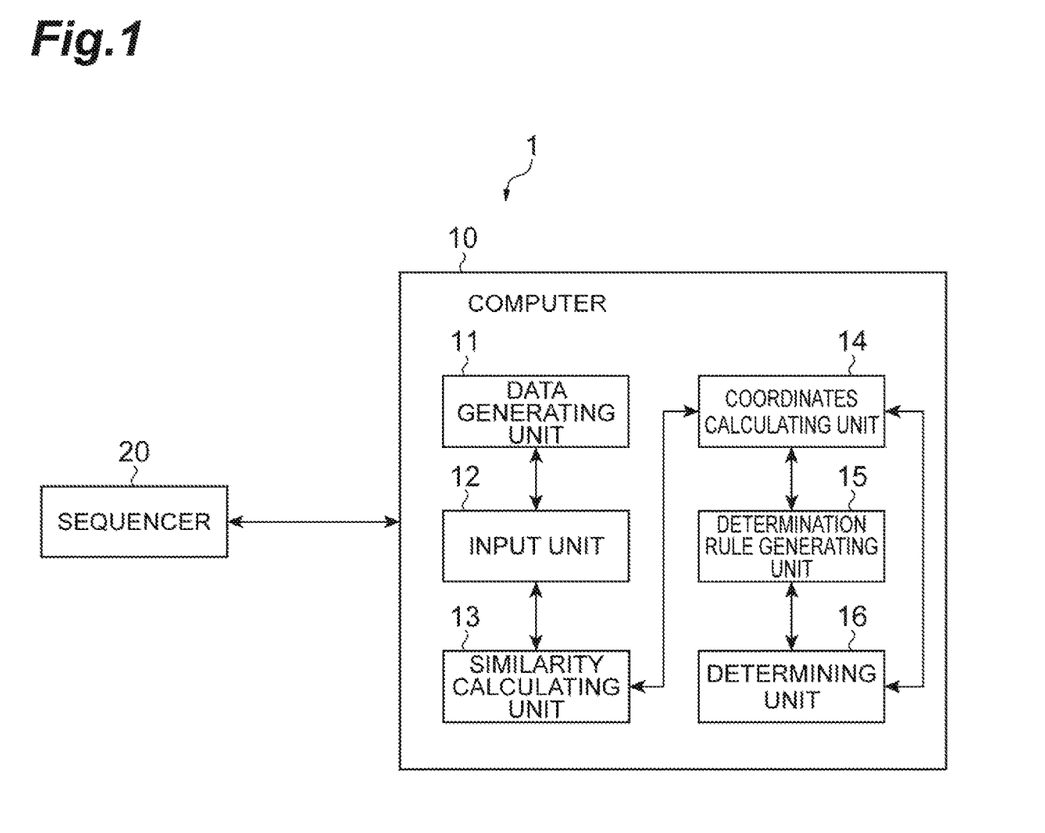
FIG. 1 is a diagram showing a configuration of a microbial community analysis system according to an embodiment of the present invention.

FIG. 1 shows a microbial community analysis system 1 according to the present embodiment. The microbial community analysis system 1 quantifies and manages states of microbial flora (bacterial flora) which are clusters of a plurality of microorganisms included in activated sludge in which a water treatment is performed. The water treatment to be an object in the present embodiment is, for example, a treatment for reducing an influence of industrial wastewater, public sewage, dirty water, or the like, which is water that is harmful to the natural environment, on the natural environment. In addition, the water treatment is performed by a water treatment system using activated sludge including microbial flora. The number of types of microorganism included in the activated sludge is generally several thousands to several tens of thousands or more. In addition, the activated sludge is generally put into a biological reaction tank (a bio tank, an activated sludge tank), and by introducing water to be treated into the biological reaction tank, the water treatment is performed. The biological reaction tank generally includes an aerobic tank and an anaerobic tank. For example, the water treatment is continuously performed according to the operation of a factory. Here, the water treatment itself is performed conventionally.

The microbial community analysis system 1 calculates coordinates in a multidimensional space indicating states of microbial flora as quantification of states of microbial flora. The coordinates are relatively determined on the basis of a similarity (similarity, β-diversity) between states of a plurality of microbial florae. When coordinates indicating states of two microbial florae are close to each other, this means that the states are similar to each other. When coordinates indicating states of two microbial florae are far from each other, this means that the states are different from each other. At least the composition of microorganisms in microbial florae (which microorganisms are included in microbial florae) is reflected in the states of microbial florae in the present embodiment.

The states of microbial flora can be managed using the coordinates. For example, states of microbial flora in activated sludge in which a water treatment is performed normally (that is, an influence of water after a water treatment on the natural environment is sufficiently small), that is, coordinates indicating states of healthy microbial flora may be stored in advance. Coordinates indicating states of microbial flora whose states are unknown are calculated, and compared with coordinates indicating states of healthy microbial flora, and thus the states of microbial flora can be determined.

The microbial community analysis system 1 generates a determination rule for determining states of microorganisms using coordinates indicating states of microbial flora. In addition, the microbial community analysis system 1 performs determination using the generated determination rule.

As shown in FIG. 1, the microbial community analysis system 1 includes a computer 10 and a sequencer 20. The computer 10 is a device configured to perform main functions of the microbial community analysis system 1, and is a device configured to calculate coordinates, generate a determination rule, and perform determination using the determination rule. Specifically, the computer 10 includes hardware such as a central processing unit (CPU), a memory, and a communication module. When these components are operated by a program or the like, functions of the computer 10 which will be described below are executed.

The sequencer 20 is reading means configured to read (determine) nucleotide sequences of genes from a plurality of microorganisms included in activated sludge. As the sequencer 20, a so-called next generation sequencer capable of reading (analyzing) genes of a plurality of microorganisms at the same time can be used. As the sequencer 20, a sequencer in the related art, for example, a GS Junior System sequencer commercially available from Roche, a GS FLX+ System sequencer commercially available from Roche, or a MiSeq System sequencer commercially available from Illumina, Inc. may be used. In addition, the sequencer 20 may read nucleotide sequences of the 16S ribosomal RNA gene as nucleotide sequences of microorganism genes. This is because the nucleotide sequence of the 16S ribosomal RNA gene is a sequence that is relatively specific for each type of microorganism. Here, in order to read the nucleotide sequence of the 16S ribosomal RNA gene, a sequence sample (sludge sample) that is collected from activated sludge and input to the sequencer 20 is prepared in advance. The activated sludge is collected from, for example, an aerobic tank and an anaerobic tank, respectively. The preparation of a sequence sample and the reading (sequencing) of nucleotide sequences can be performed, for example, as follows.

[Preparation of Microbial Flora DNA]

About 1.5 ml of a solution containing of microorganism groups is collected from activated sludge and centrifuged at room temperature (13,000 rpm×5 minutes). The supernatant is removed, 1 ml of a sterile physiological saline is then added, mixing by inversion is performed for about 5 seconds, and then centrifugation is performed at room temperature (13,000 rpm×5 minutes). After the supernatant is removed, 300 µl of a lysis buffer (commercially available from AMR Inc.) is added and suitable mixing is performed. Then, the obtained suspension is added to a tube (Easy Extract for DNA (commercially available from AMR Inc.)) containing beads, and then stirred and disintegrated using a vortex mixer for 2 minutes. 300 µl of a TE solution (10 mM Tris, 1 mM EDTA, pH 8.0) (hereinafter referred to as TE) is added to the disintegrated solution and centrifugation is performed at 4° C. (13,000 rpm×5 minutes). Then, 450 µl of the supernatant solution is put into a new tube, and 600 µl of a phenol mixture (included in Easy Extract for DNA (commercially available from AMR Inc.)) is added thereto, stirring is performed for 1 minute using a vortex, and then centrifugation is performed at 4° C. (13,000 rpm×5 minutes). 300 µl of the supernatant is collected and put into a new tube (1.5 ml), and 1200 µl of ethanol (99.5%) is added thereto and centrifugation is performed at 4° C. (13,000 rpm×5 minutes). After the supernatant is removed, 1000 µl of cold ethanol (70%) is added and centrifugation is performed at 4° C. (13,000 rpm×5 minutes). The obtained DNA pellets are dried in a vacuum and then 150 µl of TE is added to prepare a bacterial flora DNA solution.

[PCR Amplification of V3-V4 Region of 16S Ribosomal RNA Gene]

A concentration of double-stranded DNA in the bacterial flora DNA solution is measured, 50 ng of DNA is set as a template on the basis of the measurement value, and PCR is performed to amplify the V3-V4 region of the 16S ribosomal RNA gene (hereinafter referred to as 16S gene) using a universal primer set (forward primer fw357F (SEQ ID NO. 1) and a reverse primer RV926r (SEQ ID NO. 2)). For PCR, using "Premix Ex Taq Hot Start Version" (registered trademark) commercially available from TAKARA BIO Inc., 50 µl of a reaction solution containing each of the primers at 50 pmol is prepared, and preheated at 94° C. for 2 minutes, and then denaturation at 98° C.×10 seconds, annealing at 50° C.×30 seconds, and extension at 72° C.×80 seconds are repeated over 25 cycles.

The structure of a sequence of a forward primer HA13621-fw357F is shown below. The forward primer includes the adapter A sequence (indicated by the upper case letters) necessary for sequence determination in the sequencer 20 on the 5' end side, and includes a universal primer sequence fw357F (indicated by the lower case letters) that is used to anneal all 16S genes of Eubacteria on the 3' end side with a barcode sequence of 10 nucleotides specific to each specimen therebetween. The barcode sequence is used to identify samples and is a nucleotide sequence that is arbitrarily designed to correspond to the number of samples provided to the sequencer 20.

```
Adapter A sequence
                                    (SEQ ID NO. 3)
    5'-CCATCTCATCCCTGCGTGTCTCCGACTCAG-3'

Universal primer sequence fw357F
                                    (SEQ ID NO. 1)
    5'-cctacgggaggcagcag-3'
```

The role of the barcode sequence will be described. For example, when 10 specimens are analyzed at the same time, HA13621-fw357F primers having 10 different barcode sequences may be prepared and amplified by PCR for the specimens. When these are mixed and provided to the sequencer 20, if the GS FLX+System sequencer capable of obtaining 1 million data items in one operation is used, 100 barcode sequences corresponding to 100 specimens are used. Thus, it is possible to obtain sequence data of 10,000 data/specimen items in one operation.

The structure of a sequence of a reverse primer HA13619-RV926r is shown below. The reverse primer includes the adapter B sequence (indicated by the upper case letters) necessary for sequence determination in the sequencer 20 on the 5' end side and includes a universal primer sequence RV926r (indicated by the lower case letters) that is used to anneal all 16S genes of Eubacteria on the 3' end side.

```
Sequence of HA13619-RV926r
                                           (SEQ ID NO. 4)
5'-CCTATCCCCTGTGTGCCTTGGCAGTCTCAGccgtcaattccttttra
gttt-3'
```

According to PCR using the above universal primer set, DNA (about 570 nucleotides) including V3-V4 regions of 16S genes of various types of bacteria constituting the bacterial flora are amplified, and a mixture thereof can be obtained as PCR product DNA thereof.

[Generation of PCR Product and Preparation of Sequence Sample]

The PCR product DNA (a mixture of DNA including V3-V4 regions of 16S genes of various types of bacteria constituting the bacterial flora) obtained from the bacterial flora DNA are mixed and treated with a DNA cleaner (commercially available from Wako Pure Chemical Industries, Ltd.), and excess primers, substrate nucleotides, and the like are removed to purify the DNA. The purified DNA is eluted with 200 µl of TE and collected. Then, the collected purified DNA solution is subjected to agarose gel electrophoresis, and a DNA fragment of about 570 bp is cut out and extracted using a MinElute Gel Extraction Kit (commercially available from QIAGEN) to prepare DNA which will be provided to the sequencer 20. This is used as a sequence sample used for the following sequencing.

[Sequencing of 16S Gene and Evaluation of Accuracy of Sequence Data]

The above sequence sample is provided to the sequencer 20 which is a GS FLX+System sequencer (commercially available from Roche) and subjected to sequencing. The sequencing conditions, processes and the like comply with protocols specified by the manufacturer. Here, in the sequencer, one molecule of the PCR product DNA prepared above is fixed to one bead. Then, fine water droplets independently formed in an emulsion including water (including PCR primers, substrate nucleotides, and DNA synthetase for amplifying a sequence template DNA) and oil are captured in beads in one-to-one correspondence. With them, PCR is performed to amplify and prepare a sequence template DNA. Therefore, the beads to which the amplified template DNA is fixed are partitioned on a titer plate, and a signal of a sequence reaction at the partitioned position is then read. Thus, it is possible to determine nucleotide sequences of PCR product DNA (a mixture of DNA including V3-V4 regions of 16S genes of various types of bacteria constituting the bacterial flora) included in the above sequence sample at random. In addition, when the above barcode sequence in the forward primer HA13621-fw357F is set as any sequence specific to each specimen derived from the samples, it is possible to analyze bacterial flora samples of about 100 types at the same time using the GS FLX+System sequencer, and it is possible to determine sequence data of 16S genes at 2,000 to 10,000 per sample derived from a certain activated sludge within about 10 to 23 hours. That is, it is possible to comprehensively analyze bacterial flora included in activated sludge without limitation to the type of bacteria.

The above is an example of a method of preparing a sequence sample and reading nucleotide sequences. Here, the preparation of a sequence sample and the reading of nucleotide sequences may be performed by a method other than the above method. The sequencer 20 and the computer 10 are connected so that information is transmitted and received therebetween. The sequencer 20 transmits information indicating the read nucleotide sequence for each microorganism (sequence information) to the computer 10. Here, the sequence information transmitted to the computer is sequence data without change sequenced in the sequencer 20 which is so-called rough sequence data.

Subsequently, functions of the computer 10 according to the present embodiment will be described. As shown in FIG. 1 the computer 10 includes a data generating unit 11, an input unit 12, a similarity calculating unit 13, a coordinates calculating unit 14, a determination rule generating unit 15, and a determining unit 16.

The data generating unit 11 is data generating means configured to receive nucleotide sequences of a plurality of microorganisms included in activated sludge which are read by the sequencer 20 from the sequencer 20, and generate data for calculating coordinates based on the nucleotide sequences. The data for calculating coordinates is a data group including information indicating a nucleotide sequence of a gene of each of microorganisms included in activated sludge for each type of microorganism (microorganism type and bacterial type). One data group corresponds to one microbial flora, and includes information indicating a nucleotide sequence of a gene of each of all types of microorganism included in activated sludge at the same timing regarding activated sludge put into the same biological reaction tank. However, when it is difficult to strictly determine nucleotide sequences of all types thereof or the like, it is not strictly necessary to include information indicating nucleotide sequences of all types thereof, and sufficient nucleotide sequences to calculate coordinates may be included.

As data for calculating coordinates, a plurality of data groups described above are necessary. For example, regarding activated sludge put into the same biological reaction tank, data groups related to each of activated sludge at a plurality of different timings may be set as a plurality of data groups for calculating coordinates. For example, a plurality of data groups may be data items of weekly nucleotide sequences of microbial flora for a plurality of weeks. That is, a solution containing microorganism groups is collected from activated sludge every week and a data group is generated. Alternatively, data groups related to each of activated sludge put into different biological reaction tanks may be a plurality of data groups for calculating coordinates.

Each of the data groups includes only nucleotide sequences for each type of microorganism, but may include data of an abundance proportion (presence probability) of each of microorganisms. The abundance proportion is a proportion of the number of microorganisms of a type included in the activated sludge for each type of microorganism (microorganism type and bacterial type) with respect to the number of all types of microorganism included in the activated sludge. However, when it is difficult to strictly determine the proportion or the like, it is not necessary for the proportion to be strictly a proportion of the number thereof with respect to the number of all microorganisms, and it may be a proportion that is approximate enough to calculate coordinates.

For example, the data generating unit 11 generates the data as follows. The data generating unit 11 receives rough sequence data from the sequencer 20. Here, the rough sequence data received from the sequencer 20 is data about a plurality of data groups, for example, data about activated sludge at a plurality of timings. That is, sequencing is performed by the sequencer 20 so that such data is obtained.

Regarding the obtained rough sequence data (for example, about 570 nucleotides/data in the above example), the data generating unit 11 allocates each sequence to each of specific samples (corresponding to each data group of the plurality of data groups) based on barcode sequences specific to samples included in sequence data. The data generating unit 11 removes sequence data having a sequence length of less than 200 and 1000 or more, sequence data having one or more mismatches with the universal primer sequence (fw357F), and sequence data having an average quality value (25 or less) of nucleotide sequences whose sequences are determined using a quality program provided to the sequencer and extracts high accuracy data.

The data generating unit 11 provides the acquired high accuracy sequence data for operational taxonomic unit analysis (hereinafter referred to as OTU analysis) according to clustering (a threshold value of 95%, 97%, or 99% in similarity). In the OTU analysis, an operation of grouping sequence data items based on the similarity of sequence data is performed. Here, a cluster group (hereinafter referred to as OTU) of sequence data having a sequence similarity of 95% or more is detected. Here, clustering of sequence data can be performed using, for example, the freeware Uclust in the related art. OTUs can be inferred to be derived from almost the same type of bacteria (microorganism). Thus, the total number of OTUs (OTU number) obtained according to clustering is considered to be equivalent to the number of bacterial types (microorganism types) constituting the bacterial flora (microbial flora) within a detectable range. The data generating unit 11 determines representative sequence data which is nucleotide sequences representing each cluster group. Determination of representative sequence data can be performed by a method used conventionally.

In addition, the proportion of each OTU in the total number of sequence data items, that is, a bacterial type composition proportion, in other words, the above abundance proportion, can be obtained from the number of sequence data items included in each OTU. Furthermore, when a homology search for representative sequence data of each OTU is performed on the above 16S gene and a bacterial genome database, it is possible to identify belonging to known bacterial types having the highest sequence similarity, that is, a bacterial type of OTU. Here, in the present embodiment, identification of bacterial types is not necessarily required. However, since it is then possible to determine specifically which type of bacteria is included in activated sludge, it is beneficial in analysis of the determination result or the like. Here, since an OTU (cluster group) in which the number of sequence data items (a count of the number of sequences) included in data groups is very small (for example, 1, 2 or 3) is not beneficial information in many cases and serves as noise during computation, it may be excluded from data of the data groups in advance.

The data generating unit 11 sets representative sequence data of each of the cluster groups as nucleotide sequences constituting a data group. In addition, the data generating unit 11 may calculate an abundance proportion for each of the above bacterial types (nucleotide sequences) for each data group and include it in the data group as data of a abundance proportion (presence probability) of each of microorganisms. The data generating unit 11 outputs the generated plurality of data groups to the input unit 12.

The input unit 12 is input means configured to input the plurality of data groups from a data generating unit 11. The input unit 12 outputs the input data groups to the similarity calculating unit 13.

The similarity calculating unit 13 is similarity calculating means configured to calculate a similarity between data groups on the basis of nucleotide sequences included in the data groups input by the input unit 12. In addition, when data of an abundance proportion of each of microorganisms is included in the data group, the similarity calculating unit 13 may calculate the similarity between data groups on the basis of information indicating the abundance proportion. For example, the degree of similarity is higher when nucleotide sequences themselves of microorganisms included in the data group and compositions of nucleotide sequences of microorganisms (which nucleotide sequences are included in what abundance proportions) are similar to each other. The similarity calculating unit 13 calculates the similarity between two data groups. In addition, the similarity calculating unit 13 calculates the similarity for all combinations of data groups.

The calculation of the similarity can be performed by a method used conventionally, for example, UniFrac analysis. UniFrac analysis is a technique for converting the similarity between groups into a numerical value from the similarity between nucleotide sequences belonging to each group (representative nucleotide sequence belonging to each OTU) and the number of sequences for an arbitrary plurality of groups composed of data groups of nucleotide sequences (Lozupone C and Knight R: UniFrac: a new phylogenetic method for comparing microbial communities. Appl Environ Microbiol 71: 8228-8235 (2005)). UniFrac analysis can be performed using, for example, the freeware Unifrac provided from the University of Colorado.

The similarity obtained by the UniFran analysis is calculated as a phylogenetic distance (UniFrac distance) (hereinafter referred to as an inter-group similarity distance) on a phylogenetic tree. The inter-group similarity distance has a value that is smaller when the similarity between data groups increases. The similarity calculating unit 13 outputs a value of the inter-group similarity distance which is the calculated similarity between data groups to the coordinates calculating unit 14. In addition, the similarity calculating unit 13 stores information used for calculating the similarity in order to perform determination according to the determination rule. Here, the calculation of the similarity is not necessarily performed by UniFrac analysis, and it may be performed by any technique by which the similarity between data groups including a plurality of nucleotide sequences can be calculated.

The coordinates calculating unit 14 is coordinates calculating means configured to calculate coordinates in a multidimensional space of each of data groups on the basis of the similarity calculated by the similarity calculating unit 13. Here, the calculated coordinates are coordinates indicating the above states of microbial flora corresponding to each of the data groups. The coordinates of similar data groups are calculated to be close to each other, and coordinates of dissimilar data groups are calculated to be far from each other. The number of dimensions of coordinates to be calculated is set and stored in the coordinates calculating unit 14 in advance. For example, two- or three-dimensional coordinates may be calculated. It is possible to perform visualization with two- or three-dimensional coordinates and it is possible to visually check the states of microbial flora.

The calculation of coordinates can be performed by a method used conventionally, for example, multidimensional scaling (MDS). Multidimensional scaling is a method of arranging an object with coordinates in a multidimensional space based on the similarity of arbitrary criteria for the object. Multidimensional scaling can be performed using, for example, freeware (R, etc.) or a commercial program. Here, the calculation of the coordinates is not necessarily performed by multidimensional scaling, and it may be performed by any technique by which coordinates can be calculated on the basis of similarity.

Figure 2:
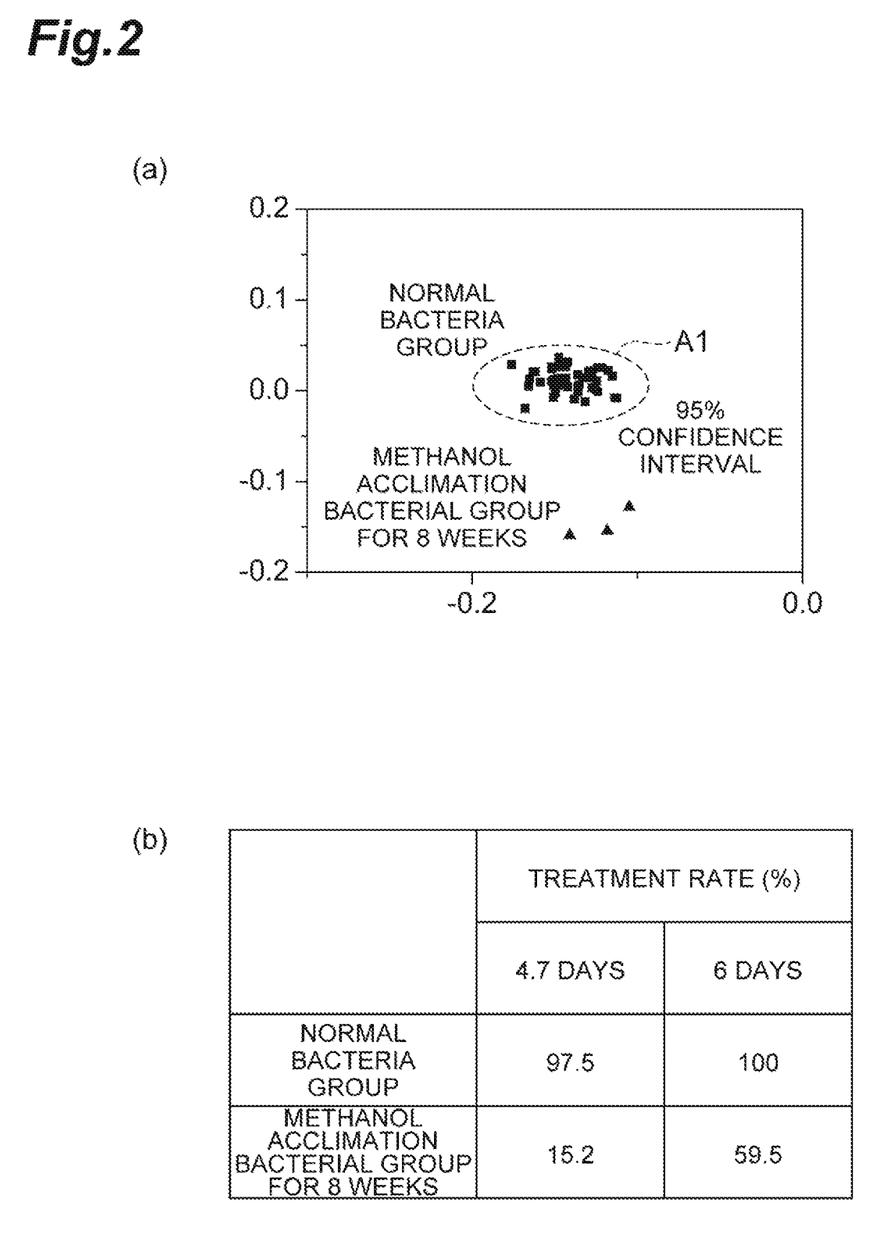
FIG. 2 is a graph showing examples of calculated coordinates in a two-dimensional space.
Figure 3:
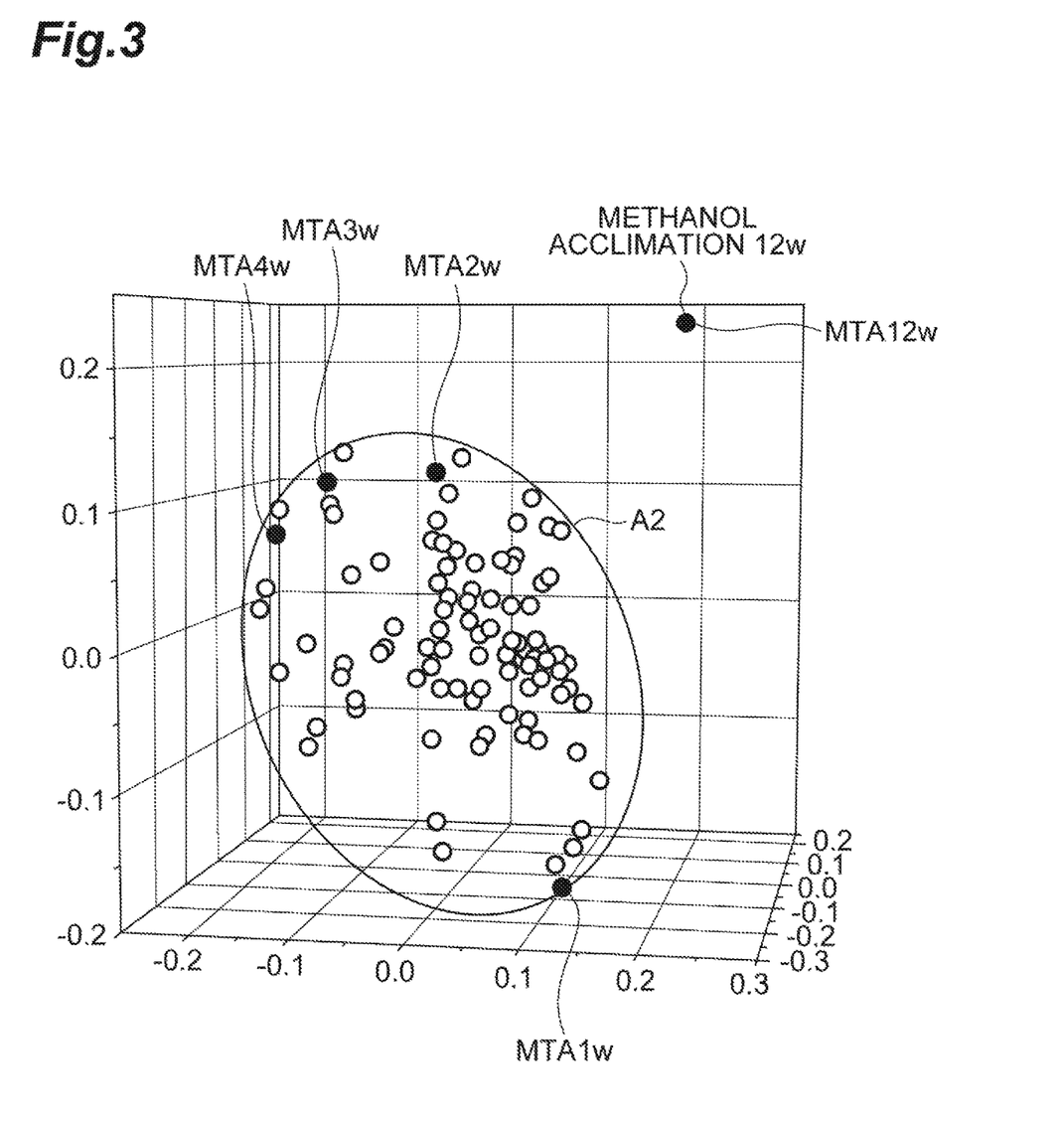
FIG. 3 is a graph showing examples of calculated coordinates in a three-dimensional space.

FIG. 2(a) and FIG. 3 show examples of graphs showing the calculated coordinates. In FIG. 2(a), coordinates are plotted in a two-dimensional space. In FIG. 3, coordinates are plotted in a three-dimensional space. Individual coordinates indicated by squares and triangles in FIG. 2 and individual coordinates indicated by circles in FIG. 3 correspond to individual data groups, that is, states of individual microbial florae. The coordinates calculating unit 14 outputs information indicating the calculated coordinates to the determination rule generating unit 15. In addition, the similarity calculating unit 13 stores information used for calculating coordinates in order to perform determination according to the determination rule.

The determination rule generating unit 15 is determination rule generating means configured to generate a determination rule for determining states of a plurality of microorganisms from a nucleotide sequence of a gene of each of the plurality of microorganisms included in activated sludge in which a water treatment is performed on the basis of the coordinates calculated by the coordinates calculating unit 14. For example, the determination rule may be used to determine whether a plurality of microorganisms, that is, microbial flora, are performing a water treatment normally. The fact that a water treatment is being performed normally means that, for example, treated water satisfies certain criteria so that an influence of water after a water treatment on the natural environment is sufficiently small. More specifically, it means that a certain proportion or more of a specific chemical substance to be treated can be treated (can decompose).

The determination rule is used to perform determination using coordinates based on a nucleotide sequence of a gene of each of microorganisms constituting determination target microbial flora. That is, the determination rule is used to perform determination using information based on data groups having the same format as the above data groups used to calculate coordinates.

When the determination rule generating unit 15 generates a determination rule, for example, microbial flora related to coordinates calculated by the coordinates calculating unit 14 in advance are set as microbial flora in which a water treatment is performed normally. That is, sets of the coordinates calculated by the coordinates calculating unit 14 correspond to clusters of microbial flora in which a water treatment is performed normally. The determination rule generating unit 15 determines a range including coordinates related to microbial flora in which a water treatment is performed normally estimated from sets of coordinates related to microbial flora in which a water treatment is performed normally for a determination rule. The determination can be performed according to determination of whether coordinates related to determination target microbial flora are included in the range. When coordinates related to determination target microbial flora are included in the range, determination target microbial flora is determined as microbial flora in which a water treatment is performed normally. On the other hand, when coordinates related to determination target microbial flora are not included in the range, it is determined that determination target microbial flora may not be microbial flora in which a water treatment is performed normally.

For example, the determination rule generating unit 15 calculates a range (for example, 95% confidence interval) in which it is estimated that a plurality of coordinates are included at a certain statistical probability (for example, 95%) or more from the plurality of coordinates related to microbial flora in which a water treatment is performed normally as a range of a determination rule. The calculation with 95% confidence can be performed by a statistical method used conventionally. The calculation with 95% confidence can be performed using, for example, freeware (R, etc.) or a commercial program.

Alternatively, when the determination rule generating unit 15 generates a determination rule, for example, microbial flora related to coordinates calculated by the coordinates calculating unit 14 in advance may include both microbial flora in which a water treatment is performed normally and microbial flora in which a water treatment is not performed normally, and these can be distinguished in the computer 10. The determination rule generating unit 15 may calculate a boundary for optimally dividing an area including coordinates related to microbial flora in which a water treatment is performed normally from an area including coordinates related to microbial flora in which a water treatment is not performed normally for a determination rule. According to the determination rule, determination can be performed according to an area in which coordinates related to determination target microbial flora are included. The calculation of the boundary can be performed by a statistical or mathematical method used conventionally.

In addition, the determination rule generating unit 15 may generate a determination rule by machine learning. The determination rule generating unit 15 outputs information indicating the generated determination rule to the determining unit 16.

The determining unit 16 is determining means configured to determine states of determination target microbial flora based on the determination rule generated by the determination rule generating unit 15. As described above, the determination rule is used to determine states of determination target microbial flora from coordinates related to the determination target microbial flora. That is, the determining unit 16 inputs information indicating coordinates related to determination target microbial flora and performs determination. The determination target is microbial flora included in activated sludge of a water treatment system (at a timing at which determination is desired to be performed). The determination target microbial flora can be microbial flora included in activated sludge of the same water treatment system (and at different timings) as the water treatment system that acquired data groups used to generate a determination rule. Alternatively, the determination target microbial flora may be microbial flora included in activated sludge of a water treatment system other than the water treatment system that acquired data groups used to generate a determination rule.

Coordinates related to determination target microbial flora are obtained in the same manner as in coordinates of individual data groups when a determination rule is generated. That is, coordinates are calculated as follows. The sequencer 20 reads base sequences of genes from a plurality of microorganisms constituting determination target microbial flora. The sequencer 20 transmits information (sequence information) indicating the read a nucleotide sequence of each of the plurality of determination target microorganisms to the computer 10.

In the computer 10, the data generating unit 11 receives sequence information from the sequencer 20, and generates data groups including information indicating a nucleotide sequence of a gene of each of the plurality of determination target microorganisms from the sequence information.

The data generating unit 11 outputs the generated data groups including information indicating nucleotide sequences of determination target microorganisms to the input unit 12. The input unit 12 inputs the data group and outputs it to the similarity calculating unit 13. The similarity calculating unit 13 inputs the data group and calculates the similarity between the data group and individual data groups used when a determination rule is generated. The similarity calculating unit 13 outputs the calculated similarity to the coordinates calculating unit 14. The coordinates calculating unit 14 calculates coordinates in a multidimensional space of a determination target data group on the basis of the similarity indicated by the information input from the similarity calculating unit 13. The calculation of the similarity and the calculation of the coordinates are performed in the same manner as when a determination rule is generated. The coordinates calculating unit 14 outputs information indicating coordinates of the determination target data group to the determining unit 16.

The determining unit 16 performs determination using coordinates indicated by the information input from the coordinates calculating unit 14 on the basis of the determination rule. For example, the determining unit 16 determines whether determination target coordinates are included in the 95% confidence interval as described above. When it is determined that determination target coordinates are included in the 95% confidence interval, the determining unit 16 determines that the determination target microbial flora is microbial flora in which a water treatment is performed normally. When it is determined that the determination target coordinates are not included in the 95% confidence interval, the determining unit 16 determines that the determination target microbial flora may not be microbial flora in which a water treatment is performed normally.

The determining unit 16 outputs the determination result. The output of the determination result is performed by, for example, displaying the determination result on a display device such as a display included in the computer 10. In addition, the output of the determination result may be performed by, for example, transmitting the determination result to another device or another module in the computer 10. Functions of the computer 10 according to the present embodiment are described above.

Figure 4:
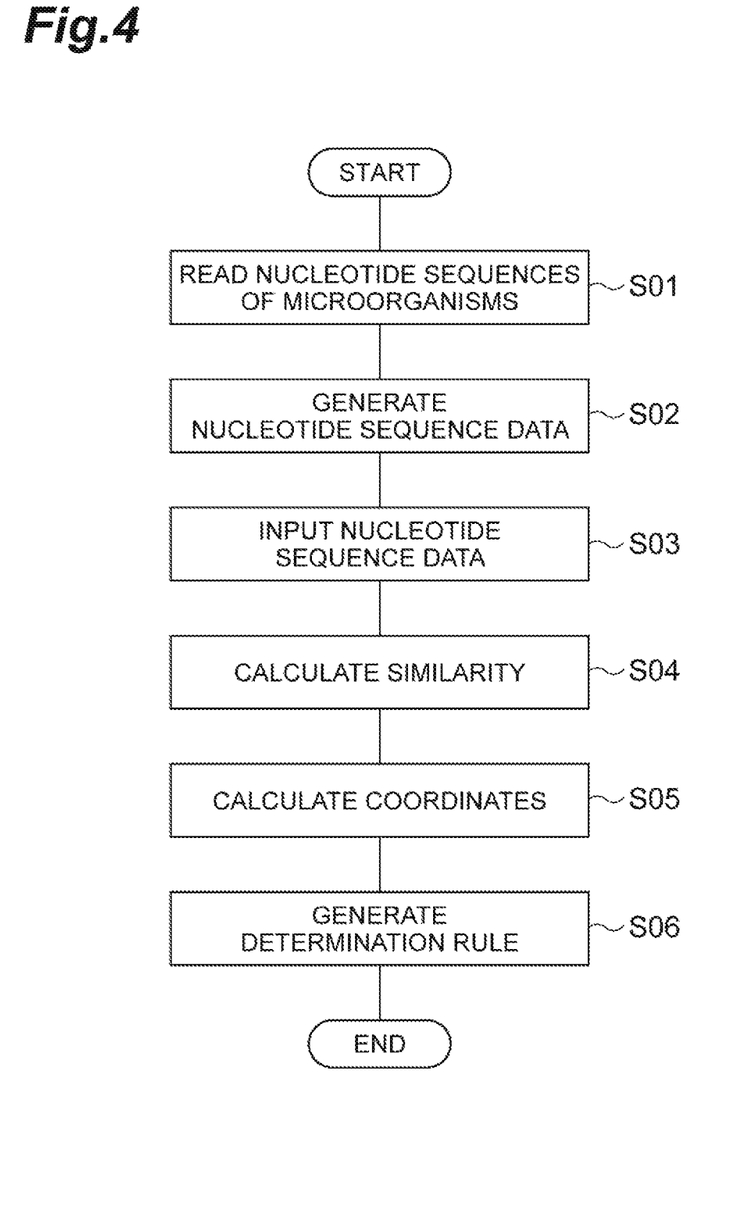
FIG. 4 is a flowchart showing processes (microbial community analysis method) performed when a microbial community analysis system according to an embodiment of the present invention generates a determination rule.
Figure 5:
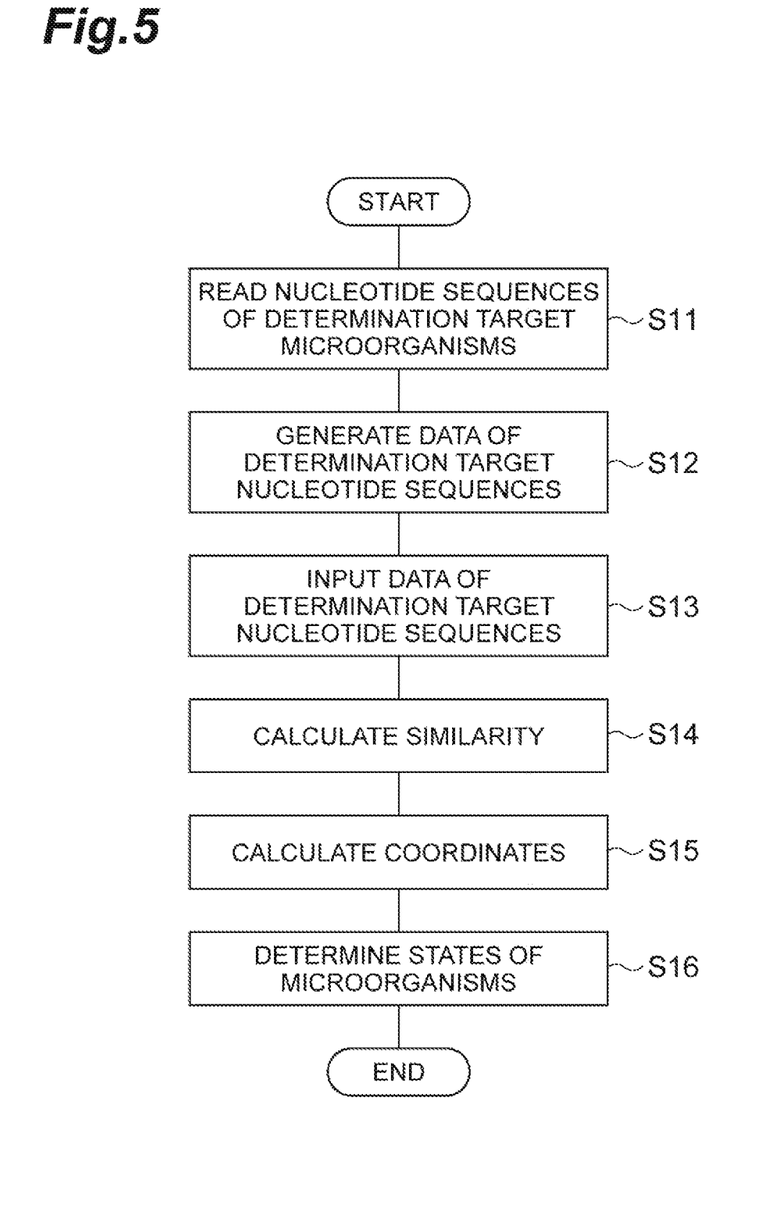
FIG. 5 is a flowchart showing processes (determination method) performed when the microbial community analysis system according to the embodiment of the present invention performs determination.

Subsequently, a microbial community analysis method and a determination method which include processes (method of operating the microbial community analysis system 1) performed by the microbial community analysis system 1 according to the present embodiment will be described with reference to flowcharts in FIG. 4 and FIG. 5. First, a process performed when a determination rule is generated will be described with reference to the flowchart in FIG. 4. In this process, first, the sequencer 20 reads nucleotide sequences of genes of microorganisms constituting microbial flora used in a water treatment system (S01, reading step). Here, nucleotide sequences of genes of microorganisms constituting microbial flora are read at a plurality of timings. The read nucleotide sequence data is output from the sequencer 20 to the computer 10.

In the computer 10, the data generating unit 11 receives nucleotide sequence data transmitted from the sequencer 20. Next, the data generating unit 11 generates a plurality of data groups including information indicating a nucleotide sequence of a gene of each of a plurality of microorganisms based on nucleotide sequence data (S02, data generating step). Next, the plurality of generated data groups or data generated so far (data groups including information indicating nucleotide sequences of genes of a plurality of microorganisms based on nucleotide sequence data of a nucleotide sequence of a gene of each of microorganisms constituting microbial flora at a plurality of timings generated previously) are input to the input unit 12 from the data generating unit 11 (S03, input step).

The plurality of input data groups are output to the similarity calculating unit 13 from the input unit 12. Next, the similarity calculating unit 13 calculates a similarity between data groups (S04, similarity calculating step). Information indicating the calculated similarity between data groups is output to the coordinates calculating unit 14 from the similarity calculating unit 13.

Next, the coordinates calculating unit 14 calculates coordinates in a multidimensional space of each of the data groups on the basis of the similarity calculated by the similarity calculating unit 13 (S05, coordinates calculating step). Information indicating the calculated coordinates is output to the determination rule generating unit 15 from the coordinates calculating unit 14. Next, the determination rule generating unit 15 generates a determination rule on the basis of the coordinates indicated by the information input from the similarity calculating unit 13 (S06, determination rule generating step). Information indicating the generated determination rule is output to the determining unit 16 from the determination rule generating unit 15. The process performed when a determination rule is generated is as described above.

Subsequently, a process performed when determination is performed will be described with reference to the flowchart in FIG. 5. In this process, first, the sequencer 20 reads nucleotide sequences of genes of microorganisms constituting microbial flora used in a water treatment system at a determination target timing (S11, reading step). The read nucleotide sequence data is output to the computer 10 from the sequencer 20.

In the computer 10, the data generating unit 11 receives the nucleotide sequence data transmitted from the sequencer 20. Next, the data generating unit 11 generates a determination target data group including information indicating a nucleotide sequence of a gene of each of a plurality of microorganisms based on the nucleotide sequence data (S12, data generating step). Next, the generated data group is input to the input unit 12 from the data generating unit 11 (S13, input step).

The input determination target data group is output to the similarity calculating unit 13 from the input unit 12. Next, the similarity calculating unit 13 calculates a similarity between the determination target data group and individual data groups used when a determination rule is generated (S14, similarity calculating step). Information indicating the calculated similarity between data groups is output to the coordinates calculating unit 14 from the similarity calculating unit 13.

Next, the coordinates calculating unit 14 calculates coordinates in a multidimensional space of the determination target data group on the basis of the similarity calculated by the similarity calculating unit 13 (S15, coordinates calculating step). Information indicating the calculated coordinates of the determination target is output to the determining unit 16 from the coordinates calculating unit 14.

Next, the determining unit 16 determines states of the determination target microbial flora from the coordinates calculated by the coordinates calculating unit 14 based on the determination rule generated by the determination rule generating unit 15 (S16, determining step). For example, information indicating the determination result is displayed so that a user can recognize the determined states. The process performed when determination is performed is as described above.

As described above, according to the present embodiment, coordinates in a multidimensional space are calculated on the basis of a nucleotide sequence of a gene of each of a plurality of microorganisms constituting microbial flora. Analysis based on nucleotide sequences is more accurate than electrophoretic analysis quantitatively and qualitatively. Thus, the coordinates calculated according to the present embodiment represent states of microbial flora accurately compared to when electrophoretic analysis is used. That is, according to the present embodiment, it is possible to analyze microbial flora accurately.

In addition, as in the present embodiment, a determination rule for determining states of microbial flora from the calculated coordinates may be generated. In such a configuration, for example, it is possible to generate a determination rule for determining whether the above microbial flora are in a normal state (healthy state). Since the coordinates calculated according to the present embodiment represent states of microbial flora accurately, it is possible to perform determination accurately according to the determination rule.

In addition, a component configured to perform determination using the determination rule generated according to the present embodiment may be included. That is, the microbial community analysis system 1 may also serve as a determination system as in the present embodiment. In such a configuration, it is possible to perform determination based on the generated determination rule. However, generation of a determination rule or determination is not necessarily always performed by the microbial community analysis system 1, and it may be performed by a device or a system other than the microbial community analysis system 1. In this case, the coordinates calculated by the microbial community analysis system 1 or the determination rule generated by the microbial community analysis system 1 is output to a determination system other than the microbial community analysis system 1. The determination system has a function of determination performed by the microbial community analysis system 1 described above.

In a biological wastewater treatment facility such as a chemical factory, during a periodic repair period of factory devices, methanol and the like are caused to flow into the biological wastewater treatment facility to maintain activated sludge. However, in a wastewater treatment after the periodic repair period, an acclimation period is necessary until the treatment is stable, and time is taken for this treatment. There are currently no management methods for measuring an end point of an acclimation period and it is difficult to determine a state in which a treatment can be performed stably and a new management method is necessary. According to the analysis and determination of the states of microbial flora in the present embodiment described above, it is easy to determine a state in which a treatment can be performed stably, and it is possible to appropriately manage microbial flora in the water treatment system.

In addition, the similarity between data groups may be calculated on the basis of abundance proportions of microorganisms as in the present embodiment. In such a configuration, coordinates can represent states of microbial flora more accurately. However, the abundance proportions are not necessarily required to calculate the similarity, and the similarity may be calculated from only nucleotide sequences.

In addition, the sequencer 20 configured to read nucleotide sequences of genes of microorganisms as in the present embodiment is included in the microbial community analysis system 1 and data groups may be generated based on the read nucleotide sequences. In such a configuration, it is possible to reliably input the nucleotide sequence data group of microorganisms and it is possible to reliably implement an embodiment of the present invention. However, the microbial community analysis system 1 does not necessarily include the sequencer 20. That is, (the input unit 12 of the computer 10 of) the microbial community analysis system 1 may input a data group from the outside.

Next, examples of coordinates indicating states of microbial flora calculated by the microbial community analysis system 1 of the present embodiment and a determination rule will be described. FIG. 2(a) shows a graph in which coordinates indicating states of microbial flora are plotted in a two-dimensional space. In FIG. 2(a), coordinates indicated by rectangles are coordinates indicating states of microbial flora (normal bacteria group) in activated sludge in which a water treatment is performed normally. Coordinates indicated by triangles are coordinates indicating states of microbial flora (methanol acclimation bacterial group for 8 weeks) in activated sludge in which microbial flora were subjected to 8 weeks of methanol acclimation and a function of a water treatment was weakened. FIG. 2(b) shows treatment rates (%) at 4.7 days and 6 days after a treatment with (S)-2-(4-chlorophenyl)-3-methylbutanoic acid on microbial flora was started.

As shown in FIG. 2(a), in a coordinates area in which coordinates corresponding to the normal bacteria group are included and a coordinates area in which the methanol acclimation bacterial group for 8 weeks are included, distinctly different coordinates areas are formed. Thus, the normal bacteria group and the methanol acclimation bacterial group for 8 weeks are clearly significantly different in at least a type of bacteria constituting the group and a structure of bacterial flora with a high or low abundance amount.

In addition, from sets of coordinates of the normal bacteria group, as shown in FIG. 2(a), an area A1 of the 95% confidence interval which is for a determination rule of the present embodiment is calculated. By determining whether coordinates indicating states of microbial flora are included in the area A1, it is possible to determine whether microbial flora are in a healthy state. In this manner, it is possible to detect a specimen that is evaluated as a poorly treated bacterial group from arbitrary specimens using the intergroup similarity distance with respect to the normal bacteria group as an index.

FIG. 3 shows a graph in which coordinates indicating states of microbial flora are plotted in a three-dimensional space. In FIG. 3, coordinates indicated by white circles are coordinates indicating states of microbial flora (normal bacteria group) in activated sludge in which a water treatment is performed normally. Coordinates indicated by black circles are coordinates indicating states of microbial flora in activated sludge in which microbial flora has been subjected to methanol acclimation and a function of a water treatment is weakened. Numerical values included in the sign of coordinates indicated by black circles represent the number of weeks for which methanol acclimation was performed. That is, MTA12w represents that methanol acclimation was performed for 12 weeks.

As shown in FIG. 3, coordinates corresponding to microbial flora in which methanol acclimation has been performed for 12 weeks are at positions far away from coordinates corresponding to the normal bacteria group. In this example also, as shown in FIG. 3, an area A2 which is for a determination rule of the present embodiment is calculated from sets of coordinates of the normal bacteria group.

REFERENCE SIGNS LIST

1 Microbial community analysis system
10 Computer
11 Data generating unit
12 Input unit
13 Similarity calculating unit
14 Coordinates calculating unit
15 Determination rule generating unit
16 Determining unit
20 Sequencer

The invention claimed is:

1. A microbial community analysis method operating a microbial community analysis system, the microbial community analysis method comprising:

generating a plurality of data groups including information indicating a nucleotide sequence of a gene of each of a plurality of microorganisms included in activated sludge in which a water treatment is performed;

calculating a similarity between each data group in the plurality of data groups on the basis of each nucleotide sequence included in the plurality of data groups;

calculating coordinates in a multidimensional space of each of the plurality of data groups on the basis of the calculated similarities;

generating, based on the calculated coordinates, at least one determination rule for determining states of microorganisms from nucleotide sequence data of the gene;

acquiring target information on a plurality of determination target microorganisms included in target activated sludge in which a water treatment is performed from at least one sample obtained from the target activated sludge in which a water treatment is performed, the

SEQUENCE LISTING

```
<160> NUMBER OF SEQ ID NOS: 4

<210> SEQ ID NO 1
<211> LENGTH: 17
<212> TYPE: DNA
<213> ORGANISM: Artificial
<220> FEATURE:
<223> OTHER INFORMATION: universal primer fw357F

<400> SEQUENCE: 1
cctacgggag gcagcag                                                              17

<210> SEQ ID NO 2
<211> LENGTH: 21
<212> TYPE: DNA
<213> ORGANISM: Artificial
<220> FEATURE:
<223> OTHER INFORMATION: universal primer RV926r

<400> SEQUENCE: 2
ccgtcaattc cttttragtt t                                                         21

<210> SEQ ID NO 3
<211> LENGTH: 30
<212> TYPE: DNA
<213> ORGANISM: Artificial
<220> FEATURE:
<223> OTHER INFORMATION: adapter A

<400> SEQUENCE: 3
ccatctcatc cctgcgtgtc tccgactcag                                                30

<210> SEQ ID NO 4
<211> LENGTH: 51
<212> TYPE: DNA
<213> ORGANISM: Artificial
<220> FEATURE:
<223> OTHER INFORMATION: reverse primer HA13619-RV926r

<400> SEQUENCE: 4
cctatcccct gtgtgccttg gcagtctcag ccgtcaattc cttttragtt t                         51
``` target information comprising a nucleotide sequence of a gene of each of the plurality of determination target microorganisms, wherein the target activated sludge is undergoing an acclimation;

generating a determination target data group based on the nucleotide sequence of a gene of each of the plurality of determination target microorganisms;

calculating a similarity between the determination target data group and each of the plurality of data groups;

calculating coordinates in a multidimensional space of the determination target data group based on the calculated similarity between the determination target data group and each of the plurality of data groups;

determining at least one state of a plurality of states of the plurality of determination target microorganisms from the calculated coordinates of the determination target data group, wherein the at least one determined state of the plurality of determination target microorganisms is determined based on the at least one determination rule, and the at least one determined state indicates acclimation is completed;

discharging water to be treated into a biological reaction tank containing the target activated sludge in which a water treatment is performed after it is determined that the acclimation is completed.

2. The microbial community analysis method according to claim 1, wherein the information on the plurality of data groups is acquired at a plurality of time points, such that information on each group is acquired at a different time point.

3. The microbial community analysis method according to claim 1, wherein the information on the plurality of data groups is acquired from at least two different biological reaction tanks.

4. The microbial community analysis method according to claim 1, wherein the at least one determination rule is generated using machine learning.

5. The microbial community analysis method according to claim 1, further comprising generating, on a computer display, a graphical representation of the at least one determined state of the plurality of determination target microorganisms, wherein the at least one determined state comprises at least two states, and wherein the graphical representation includes a representation of states of the at least two states differently from one another.

6. The microbial community analysis method according to claim 1, wherein the plurality of states comprise one or more of a healthy state, a state indicating a time that has elapsed since a beginning of the acclimation, and a state indicating an end point of the acclimation.

7. The microbial community analysis method according to claim 1, wherein the coordinates in the multidimensional space of each of the plurality of data groups are calculated using a multidimensional scaling.

8. The microbial community analysis method according to claim 1, wherein the at least one determination rule comprises a range of coordinates related to microbial flora in which a water treatment is performed normally.

* * * * *